(12) United States Patent
Jacobs et al.

(10) Patent No.: US 12,201,540 B2
(45) Date of Patent: Jan. 21, 2025

(54) HYDRAULIC LOCKING DEVICE AND SYSTEMS

(71) Applicant: Motion Control, Inc., Salt Lake City, UT (US)

(72) Inventors: Gregory James Jacobs, Salt Lake City, UT (US); Edwin Kay Iversen, Salt Lake City, UT (US); Carter J. Greene, West Valley City, UT (US); Jeffery David Christenson, West Valley City, UT (US)

(73) Assignee: Motion Control, Inc., Salt Lake City, UT (US)

( * ) Notice: Subject to any disclaimer, the term of this patent is extended or adjusted under 35 U.S.C. 154(b) by 565 days.

(21) Appl. No.: 17/507,538

(22) Filed: Oct. 21, 2021

(65) Prior Publication Data

US 2023/0131100 A1    Apr. 27, 2023

(51) Int. Cl.
| | |
|---|---|
| *A61F 2/74* | (2006.01) |
| *F16F 9/34* | (2006.01) |
| *A61F 2/50* | (2006.01) |
| *A61F 2/68* | (2006.01) |

(52) U.S. Cl.
CPC ...... *A61F 2/748* (2021.08); *A61F 2002/5006* (2013.01); *A61F 2002/6854* (2013.01)

(58) Field of Classification Search
CPC .... A61F 2/748; A61F 2/74; A61F 2002/5006; A61F 2002/6854; F16F 9/466; F16F 9/34
See application file for complete search history.

(56) References Cited

U.S. PATENT DOCUMENTS

| | | | | |
|---|---|---|---|---|
| 6,113,642 | A * | 9/2000 | Petrofsky | F16F 9/46 188/282.3 |
| 7,942,935 | B2 * | 5/2011 | Iversen | A61F 2/6607 623/25 |
| 8,597,369 | B2 | 12/2013 | Hansen et al. | |
| 8,915,969 | B2 * | 12/2014 | Boender | A61F 2/605 623/44 |
| 9,549,827 | B2 | 1/2017 | Hansen et al. | |
| 10,105,243 | B2 | 10/2018 | Hansen et al. | |
| 10,376,388 | B2 | 8/2019 | Hansen et al. | |
| 2003/0106753 | A1 * | 6/2003 | Nezu | B60G 17/08 188/316 |

(Continued)

FOREIGN PATENT DOCUMENTS

EP    4226898 A1 *  8/2023  ............... A61F 2/64

*Primary Examiner* — Thomas W Irvin
(74) *Attorney, Agent, or Firm* — Foley & Lardner LLP

(57) ABSTRACT

Technology is described to provide a locking device to control movement of a prosthetic limb. The technology may include a hydraulic damper having a movable damper wall in a hydraulic housing of the hydraulic damper, and the movable damper wall may form a first chamber and second chamber in the hydraulic damper. A first fluid channel may be coupled to the first chamber. In addition, a latch may be in fluid communication with the first fluid channel. A poppet valve can be configured to set the latch in an open position when pressure is reduced in the first chamber and to stop fluid movement when pressure is increased in the first chamber. A second fluid channel between the second chamber and the latch may enable fluid to flow between the second chamber and the latch.

21 Claims, 5 Drawing Sheets

(56) References Cited

U.S. PATENT DOCUMENTS

| | | | |
|---|---|---|---|
| 2006/0231359 A1* | 10/2006 | Matsunaga | B60G 17/0152 188/313 |
| 2006/0235544 A1* | 10/2006 | Iversen | A61F 2/70 623/47 |
| 2011/0307078 A1* | 12/2011 | Boender | F16F 9/512 623/26 |
| 2014/0216871 A1* | 8/2014 | Shibahara | F16F 9/348 188/313 |
| 2016/0235558 A1* | 8/2016 | Boender | A61F 2/604 |
| 2022/0304832 A1* | 9/2022 | Will | A61F 2/60 |
| 2023/0125274 A1* | 4/2023 | Iversen | A61F 2/70 623/52 |

\* cited by examiner

HYDRAULIC LOCKING DEVICE AND SYSTEMS

BACKGROUND

Prostheses (or prosthetics) are artificial devices that replace body parts (e.g., fingers, hands, arms, legs). Generally, prostheses may be used to replace body parts lost by injury, disease or missing from birth.

In one example, an intact human foot, connected to the ankle, travels through stance and swing phases of a gait cycle during each stride of motion, whether the motion involves walking, jogging, or running. By adjusting the stiffness and damping characteristics of a prosthetic foot and ankle mechanism, the springiness of the intact natural human foot and the corresponding damping of natural human joints may be mimicked, thereby optimizing the prosthesis for the desired motion of the wearer. However, the characteristics that are desired to store and release energy appropriately for walking tend to oppose those best suited to fast walking and running.

DETAILED DESCRIPTION

Figure 1:
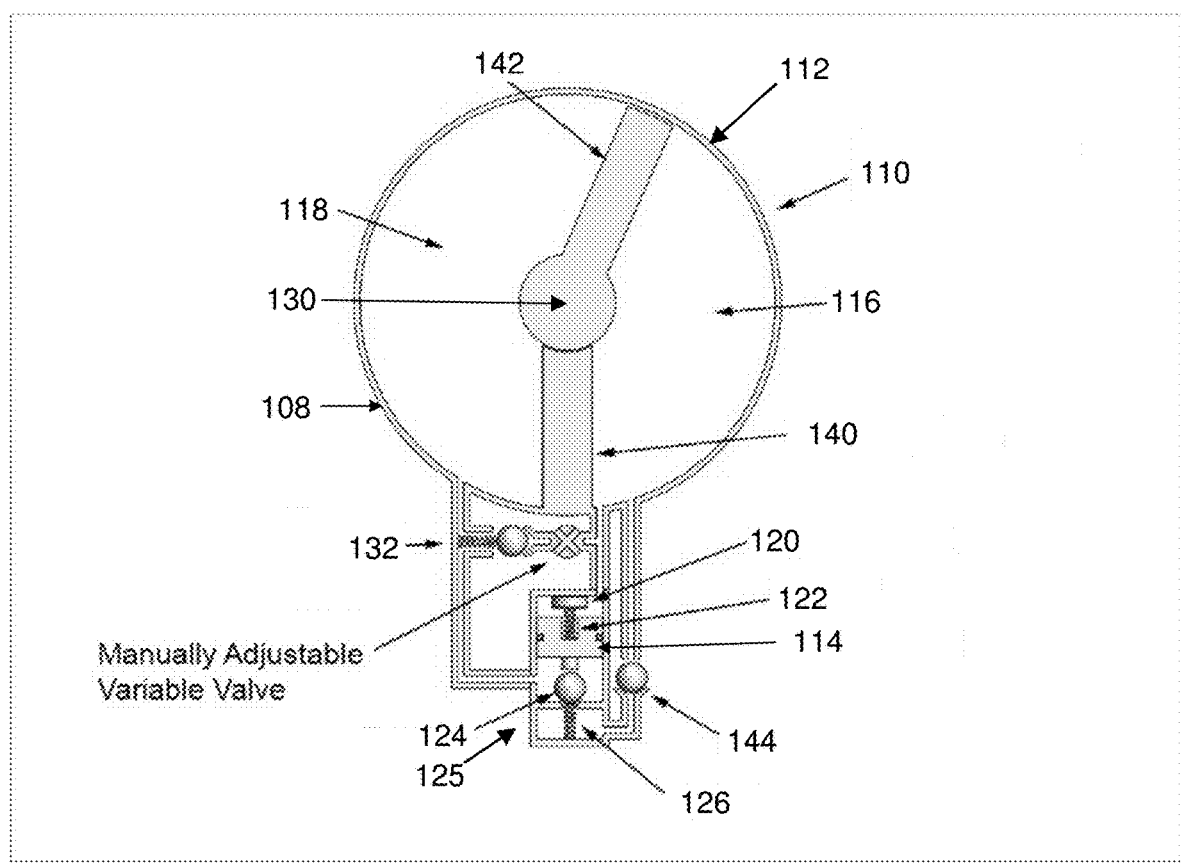
FIG. 1 illustrates an example of a magnetic locking mechanism to control a prosthetic or orthotic joint, as coupled with a rotary hydraulic damper.

Reference will now be made to the examples illustrated in the drawings, and specific language will be used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure are to be considered within the scope of the description.

A technology is described for use in orthotics and prosthetics, such as prosthetic joints. The technology can freely allow joint motion in one direction but the joint may lock once the joint motion is reversed. When the joint is subsequently unloaded, the joint can unlock. In the unlocked direction, the joint may be spring loaded to move in the previously locked direction or the joint may just be free to move.

In the past, many mechanisms have been used to achieve the purpose of free movement in one direction and locking in a reverse direction in the prosthetics area with little or limited success. These mechanisms may have included: ratchets, cams, sprags or other braking systems. Such mechanisms are noisy, heavy, and susceptible to wear during cyclic heavy loading. In contrast, this technology may enable a prosthetic or orthotic joint to behave in a useful way (e.g., free movement in one direction while locking for a limited time in the opposite direction) while eliminating the problems found in past devices or systems.

This locking mechanism may be used in several orthotic or prosthetic configurations, such as: elbow prostheses, orthotic elbows, prosthetic knees, orthotic knees, prosthetic ankles, and/or orthotic ankles. Further, this technology may be used in other types of medical joint or prosthetics applications.

The locking joint may contain a hydraulic mechanism or system which enables the described functionality. This locking device or mechanism may include a hydraulic system that has two chambers that are connected by one or more fluid pathways (e.g., two fluid pathways). The fluid pathways may be tubes, conduits, channels, pipes or similar fluid transporting pathways. These pathways may contain one or more valves that can limit or stop the hydraulic fluid from flowing between the two chambers of the hydraulic system or locking device. As the joint articulates, fluid may flow through these pathways and valves.

When the valves are partially closed, resistance to articulation of the joint occurs. When the valves are totally closed, articulation of the joint is stopped, and the joint is locked. Check valves may be positioned in each pathway such that a first pathway may limit or lock motion in one direction and a second pathway may limit or lock motion in the other direction.

This hydraulic system or mechanism may mechanically and/or magnetically respond (e.g., mechanically and/or magnetically sense) when the joint moves in a first specified direction and then mechanically and/or magnetically lock the joint in a hydraulic manner to movement in the other direction. Furthermore, the system may respond mechanically and/or magnetically when the joint is loaded and unloaded in the locked direction. When the joint is unloaded, the lock may automatically unlock and allow free motion of the joint in the previously locked direction.

FIG. 1 illustrates a schematic of a lock mechanism used with a rotary hydraulic damper 110 that may control a prosthetic or orthotic joint. For example, the housing 112 and stationary wall 140 of the rotary hydraulic damper 110 may be connected to a socket of an individual with transhumeral limb loss and the moving wall 142 may be connected to the prosthetic forearm. Alternatively, these connections to the prosthetic socket and prosthetic forearm may be switched. As a result, a revolute joint 130 may be created between a stationary wall 140 and a moving wall 142 of the rotary hydraulic damper 110. The stationary wall 140 and moving wall 142 of the rotary hydraulic damper may also be described as a stationary vane and a moving vane.

Alternatively, the hydraulic damper may be a linear hydraulic damper. In a hydraulic damper, a damper wall in a hydraulic housing (e.g., hydraulic cylinder) may be a vane or a piston that forms at least two chambers in the hydraulic housing.

This device or system can use a sense piston 114 in fluid communication with two hydraulic chambers (e.g., chamber A 118 and/or chamber B 116). The sense piston 114 may be made from metal, ferromagnetic material, and/or have one or more magnets embedded in the sense piston 114. This sense piston 114 can control the locking in the counterclockwise direction of the joint (e.g., counterclockwise movement of the moving wall 142 illustrated in FIG. 1). As the moving wall 142 or vane is moved in the clockwise direction, the pressure in chamber B 116 created by the moving wall 142 reaches a set level, causing the sense piston 114 to be forced away from the magnet latch 120 into the locked position. In the locked position, the sense piston 114 is spring loaded by a first spring or first spring 122 (i.e., spring one) against a poppet valve 125. In this position, the joint is locked against moving in the counterclockwise direction. When the joint is loaded in the locked counterclockwise direction, the joint remains locked.

Loading the joint in the clockwise direction causes the joint to unlock. The clockwise loading of the joint produces pressure in chamber A 118 that causes the sense piston 114 to be forced back into the magnetically latched position with the magnetic latch 120. For example, the sense piston 118 maybe forced against or touching the magnetic latch 120. Alternately, the sense piston 118 may simply be in magnetic proximity to the magnetic latch 120 so magnetic attraction force holds the sense piston 118 near the magnetic latch 120 as balanced by the forces of the first spring 122. In the latched position, the poppet valve 125 is unlocked using the second spring 126, as soon as the joint is unloaded. Accordingly, fluid may then flow through the poppet valve 125.

When the joint is unlocked, a spring in the system (e.g., in the linear cylinder or around the revolute joint) can be positioned such that the joint can be automatically moved in the counterclockwise direction and restored to the initial position. Thus, a joint may return to an original position without the amputee having to move the joint to the starting position.

Figure 2:
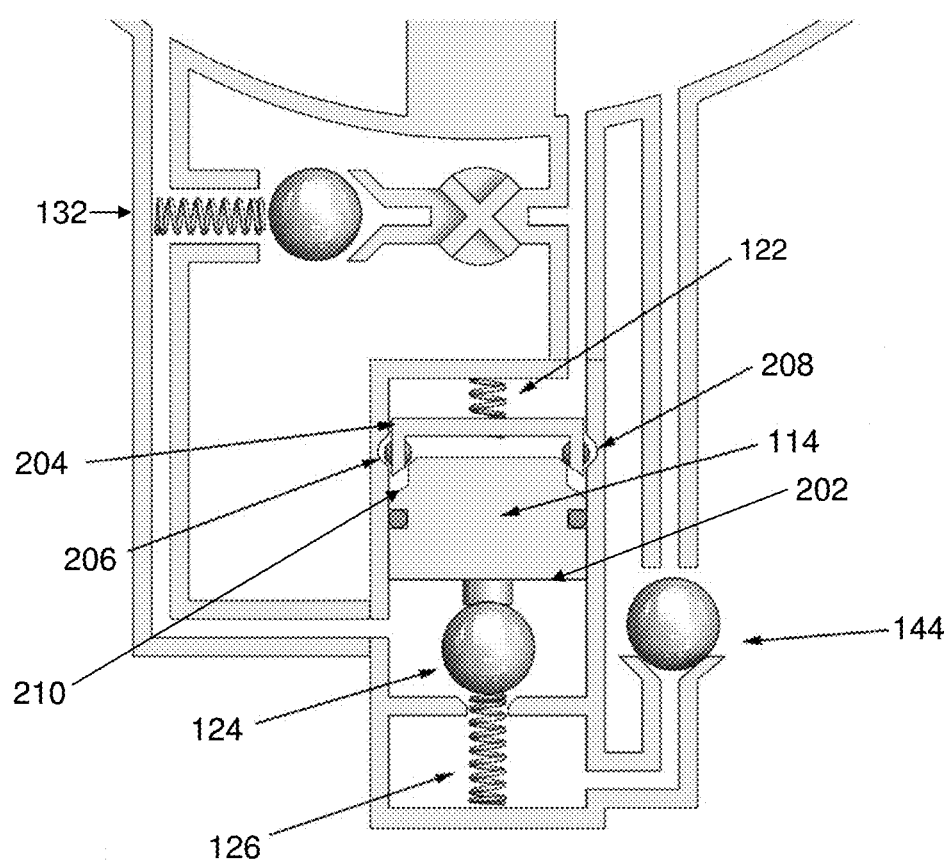
FIG. 2 is a diagram illustrating an example of a locking mechanism that uses a ball detent configuration.

FIG. 2 illustrates a ball detent mechanism that is an alternative to the magnetic detent illustrated in FIG. 1. When the moving wall of the joint is moved counterclockwise, pressure in chamber A (118 in FIG. 1) is routed to a first piston face 202 (e.g., the "bottom" face in FIG. 2) of the sense piston 114 which forces the sense piston 114 away from the poppet valve 125 (upward to the top of the page in FIG. 2) and the moves the detent ball cage 204 upward and compresses the first spring 122 or detent cage spring. The detent balls 206 can be pushed into the annular detent grooves 208 by a chamfer 210 on the sense piston 114. This movement latches the detent ball cage 204 and detent balls 206 and eliminates locking force (e.g., a downward locking force in FIG. 2) on the poppet valve 125 and past the poppet valve ball 124.

The ball detent latching mechanism, as described for FIG. 2 above, includes a detent ball cage 204, detent balls 206, and an annular detent groove 208. Load pressure forces the sense piston 114 and detent ball cage 204 against the first spring 122 (e.g., spring one) into the latched position. As the sense piston 114 is being forced into the latched position, an incline (e.g., a chamfer) on the sense piston 114 forces the detent balls 206 radially into the annular detent groove 208 through holes (e.g., square slots, round holes, etc.) in the detent ball cage 204. These detent balls 206 latch the sense piston 114 and detent ball cage 204 in the latched position against the first spring 122 (e.g., spring one) until pressure forces the sense piston 114 down and releases the detent balls 206.

When used in a prosthetic or orthotic elbow, the device or mechanism may operate in various ways, for example: when the elbow is actuated by a cable attached to the opposite intact shoulder joint, the arm will lift as soon as the pressure created in chamber B by using the cable exceeds the pressure relief valve pressure. When the force on the cable is released, the elbow is locked in extension. When the cable is again pulled and the load is released from the arm, the elbow is unlocked and is able to extend.

As another example, when used in a prosthetic ankle, the mechanism may perform as follows: at heel strike, the ankle can plantar flex and the pressure in chamber B 116 may exceed the pressure needed to open the pressure relief valve 132 or pressure relief check valve. A second check valve 144 may be positioned in a second pathway that the second pathway may limit or lock fluid flow and motion in the other direction.

The mechanism can then allow the ankle to plantar flex. If the ankle moves even a small amount in the dorsi-flexion direction, the ankle is locked in the dorsi-flexion direction but is free to plantar flex. This allows the ankle to adapt to any incline by plantar flexing the ankle until the foot is flat on the ground. The prosthesis user can then load the dynamic toe sole plate until toe-off. As soon as the toe is unloaded, the second spring 126 (e.g., spring two) lifts the poppet valve 125 (e.g., poppet valve ball 124) and unlocks the ankle. A toe-lift spring can then dorsi-flex the toe to allow for ground clearance during the swing phase of the gait cycle.

The latching mechanism can be magnetic latching as shown schematically in FIG. 1 or a ball detent as shown in FIG. 2. Other configurations of magnet latches or detent ball types of latching systems may also be used in prosthetic and orthotic applications.

Figure 3:
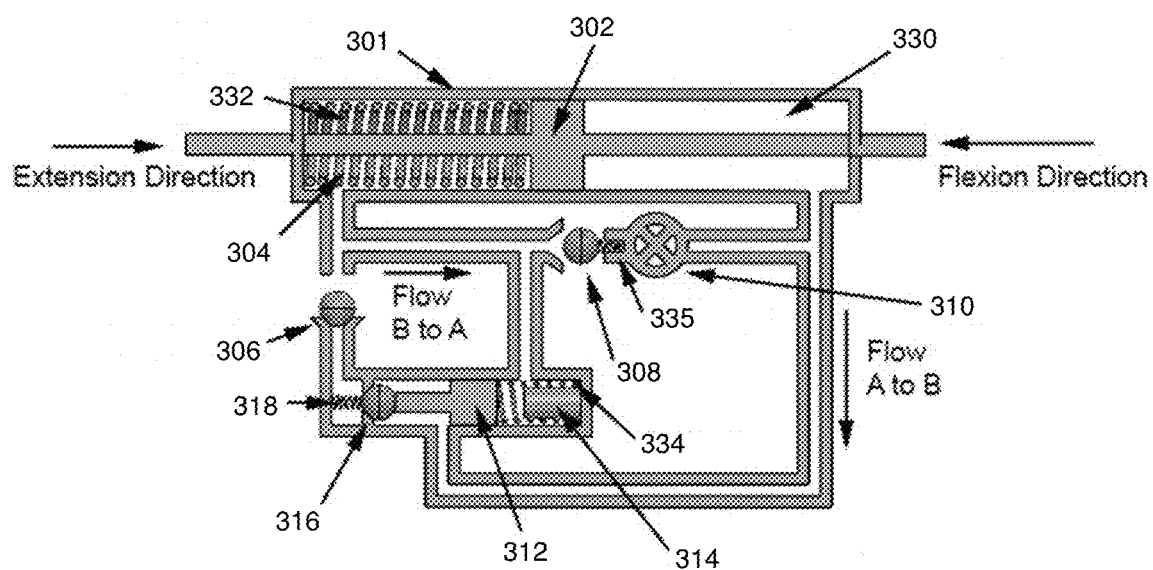
FIG. 3 is a schematic diagram illustrating an example of a locking mechanism in the locked position.
Figure 4:
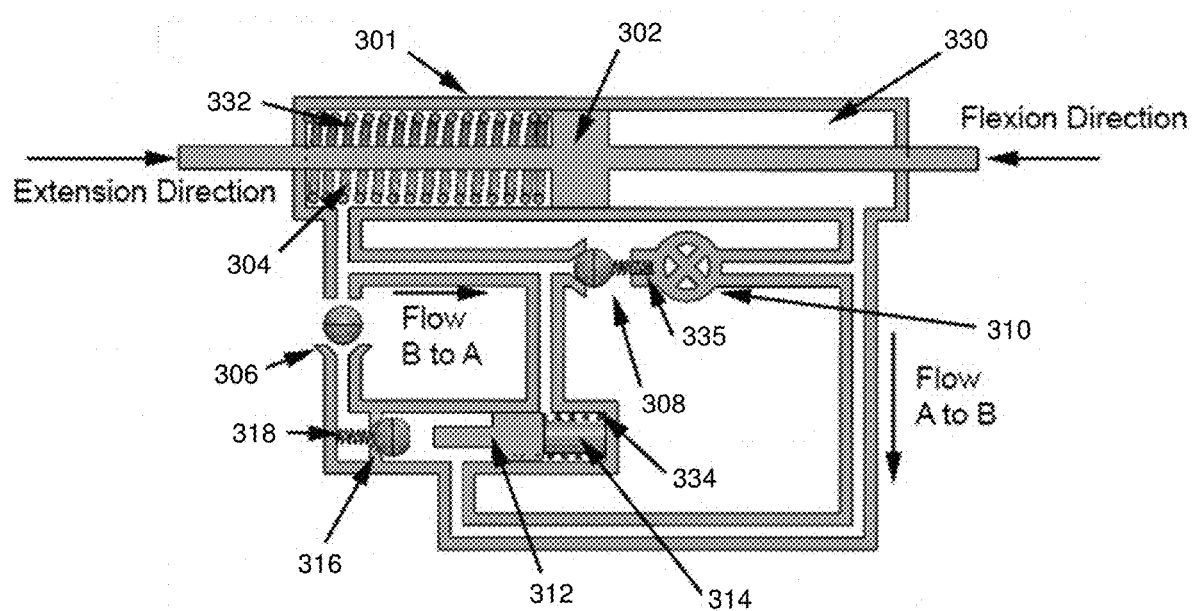
FIG. 4 is a schematic diagram illustrating an example of the extension locking mechanism in the locked and loaded position.
Figure 5:
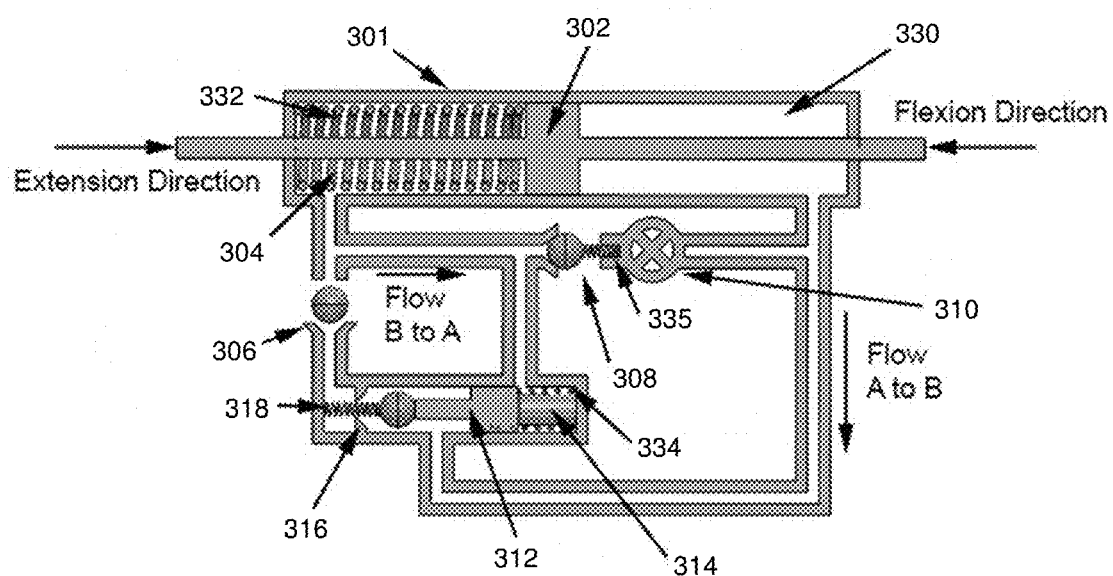
FIG. 5 is a schematic diagram illustrating an example of the extension locking mechanism in the unloaded, unlocked position.

FIGS. 3 through 5 are schematic diagrams illustrating the locking mechanism as the locking mechanism moves through the locked, locked/loaded, and unloaded/unlocked positions. FIG. 3 illustrates an example of the locking mechanism in the locked position. When a prosthetic or orthotic joint is flexed, the hydraulic piston 302 in the hydraulic cylinder 301 is forced to a first position (e.g., forced to the left in FIG. 3) producing a pressure in chamber B 304. This pressure closes the check valve 306 and opens the pressure relief valve 308 that is biased by spring four 335 or a check valve spring, when a defined pressure is reached. Hydraulic fluid then flows through the manual valve 310. The manual valve 310 is manually opened or closed by a user (e.g., an amputee or medical professional) to set a defined resistance to the joint motion. The pressure in chamber B 304 also forces the sense piston 312 away from the magnetic latch 314 and forces the locking poppet valve 316 against spring two 318 (e.g., the poppet spring) into a locked position.

FIG. 4 illustrates the extension locking mechanism in the locked and loaded position. When the prosthetic joint is extended, the hydraulic piston 302 is forced to a second position (e.g., toward the right in FIG. 4) producing a pressure in chamber A 330. This pressure closes the pressure relief valve 308, produces locking pressure on the locking poppet valve 316 and forces the sense piston 312 against magnetic latch 314 (e.g., magnet) into the latched position. In the case of a prosthetic foot joint, the joint is thereby locked in the extension direction until the foot is unloaded.

FIG. 5 illustrates the extension locking mechanism in the unloaded, unlocked position. When the locked joint is unloaded, the pressure in Chamber A 330 drops to a pressure that allows spring two 318 (or the poppet spring) to open the locking poppet valve 316. The unloaded pressure in chamber A 330 may be produced by the force from spring one 332 (e.g., a cylinder spring) on the hydraulic piston 302. Spring two 318 (or the poppet spring) may have sufficient force to open the locking poppet valve 316 in the presence of the unloaded pressure in chamber A 330. In particular, the force provided by spring three 334 is desired to be less than the force of spring two 334, so that the sense piston 312 remains latched as pressure in chamber A 330 drops. In addition, when the locking poppet valve 316 is opened by spring two 318, the joint is now unlocked to extend. Spring one 332 may then force the hydraulic piston 302 to the right thereby extending the joint.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

The invention claimed is:

1. A device to control movement of a prosthetic joint or an orthotic joint, comprising:
   a hydraulic damper having a movable damper wall in a hydraulic housing of the hydraulic damper, wherein the movable damper wall forms a first chamber and second chamber in the hydraulic damper;
   a first fluid channel coupled to the first chamber;
   a latch in fluid communication with the first fluid channel;
   a poppet valve configured to set the latch in an open position when pressure is reduced in the first chamber and to stop fluid movement when pressure is increased in the first chamber; and
   a second fluid channel between the second chamber and the latch, which enables fluid to flow between the second chamber and the latch.

2. The device as in claim 1, wherein the hydraulic damper is a linear hydraulic damper.

3. The device as in claim 1, wherein a revolute joint is formed using the movable damper wall in the hydraulic housing of a rotary hydraulic damper.

4. The device as in claim 1, wherein the latch is a magnetic latch with a fixed magnet to hold a sense piston in an open position when pressure is reduced in the first chamber.

5. The device as in claim 1, wherein the poppet valve includes a poppet ball and poppet spring.

6. The device as in claim 1, wherein the latch includes a detent ball cage and detent balls attached to a detent spring.

7. The device as in claim 6, further comprising a detent groove in a wall of a latch chamber.

8. The device as in claim 1, wherein the latch is set in latch position by the poppet valve when pressure in the first chamber is reduced.

9. The device as in claim 1, further comprising a third fluid flow channel with a check valve that allows fluid flow from the second chamber to the first chamber when the latch is in an open position.

10. The device as in claim 1, further comprising a pressure relief valve between a first fluid flow channel and a second fluid flow channel.

11. A locking device to control movement of a prosthetic joint or an orthotic joint, comprising:
    a hydraulic damper having a movable damper wall in a hydraulic housing of the hydraulic damper, wherein the movable damper wall forms a first chamber and second chamber in the hydraulic damper;
    a revolute joint for a prosthetic limb that is formed using the movable damper wall in the hydraulic housing;
    a first fluid channel coupled to the first chamber;
    a magnetic latch in fluid communication with the first fluid channel and having a fixed magnet to hold a sense piston in an open position when pressure is reduced in the first chamber;
    a poppet valve configured to set a latch in an open position when pressure is reduced in the first chamber and to stop fluid movement between the first chamber and the second chamber when pressure is increased in the first chamber; and
    a second fluid channel in fluid communication between the second chamber and the latch, wherein the second fluid channel enables fluid to flow between the second chamber and the latch.

12. The locking device as in claim 11, wherein the hydraulic damper is a rotary hydraulic damper.

13. The locking device as in claim 11, wherein the poppet valve includes a poppet ball and poppet spring.

14. The locking device as in claim 11, wherein the latch is set in latch position by the poppet valve when pressure in the first chamber is reduced.

15. The locking device as in claim 11, further comprising a third fluid flow channel with a check valve that allows fluid flow from the second chamber to the first chamber when the latch is in an open position.

16. The locking device as in claim 11, further comprising a pressure relief valve between a first fluid flow channel and a second fluid flow channel.

17. A locking device to control movement of a prosthetic joint or an orthotic joint, comprising:
    a hydraulic damper having a movable damper wall in a hydraulic housing of the hydraulic damper, wherein the movable damper wall forms a first chamber and second chamber in the hydraulic damper;
    a revolute joint for a prosthetic limb that is formed using the movable damper wall in the hydraulic housing;
    a first fluid channel coupled to the first chamber;
    a latch in fluid communication with the first fluid channel, wherein the latch includes a detent ball cage, detent balls attached to a detent spring and a detent groove in a wall of a latch chamber;
    a poppet valve configured to set the latch in an open position when pressure is reduced in the first chamber and to stop fluid movement between the first chamber and second chamber when pressure is increased in the first chamber; and
    a second fluid channel in fluid communication between the second chamber and the latch, wherein the second fluid channel enables fluid to flow between the second chamber and the latch.

18. The locking device as in claim 17, wherein the hydraulic damper is a rotary hydraulic damper.

19. The locking device as in claim 17, wherein the poppet valve includes a poppet ball and poppet spring.

20. The locking device as in claim 17, wherein the latch is set in latch position by the poppet valve when pressure in the first chamber is reduced.

21. The locking device as in claim 17, further comprising a third fluid flow channel with a check valve that allows fluid flow from the second chamber to the first chamber when the latch is in an open position.

* * * * *